(12) United States Patent
Tachibana et al.

(10) Patent No.: US 10,988,427 B2
(45) Date of Patent: Apr. 27, 2021

(54) OLEFIN AND METHANOL CO-PRODUCTION PLANT AND OLEFIN AND METHANOL CO-PRODUCTION METHOD

(71) Applicant: Mitsubishi Heavy Industries Engineering, Ltd., Kanagawa (JP)

(72) Inventors: Shinya Tachibana, Tokyo (JP); Akiyori Hagimoto, Tokyo (JP)

(73) Assignee: Mitsubishi Heavy Industries Engineering, Ltd., Kanagawa (JP)

( * ) Notice: Subject to any disclaimer, the term of this patent is extended or adjusted under 35 U.S.C. 154(b) by 0 days.

(21) Appl. No.: 16/760,633

(22) PCT Filed: Dec. 14, 2017

(86) PCT No.: PCT/JP2017/044831
§ 371 (c)(1),
(2) Date: Apr. 30, 2020

(87) PCT Pub. No.: WO2019/116484
PCT Pub. Date: Jun. 20, 2019

(65) Prior Publication Data
US 2020/0347000 A1 Nov. 5, 2020

(51) Int. Cl.
| | | |
|---|---|---|
| *B01J 8/00* | (2006.01) | |
| *B01J 8/02* | (2006.01) | |
| *B01J 8/04* | (2006.01) | |
| *B01J 19/24* | (2006.01) | |
| *C01B 3/34* | (2006.01) | |

(Continued)

(52) U.S. Cl.
CPC ......... *C07C 29/1518* (2013.01); *B01J 19/245* (2013.01); *B01J 19/2445* (2013.01);
(Continued)

(58) Field of Classification Search
CPC ......... B01J 8/00; B01J 8/02; B01J 8/04; B01J 8/0496; B01J 19/00; B01J 19/24;
(Continued)

(56) References Cited

U.S. PATENT DOCUMENTS

| 5,736,107 A | 4/1998 | Inomata et al. |
| 5,750,821 A | 5/1998 | Inomata et al. |

(Continued)

FOREIGN PATENT DOCUMENTS

| JP | H07-88314 B2 | 9/1995 |
| JP | H08-157395 A | 6/1996 |

(Continued)

OTHER PUBLICATIONS

Twenty-First European Symposium on Computer Aided Process Engineering, 2011, 1874-1878, Computer Aided Chemical Engineering vol. 29 (5 pages).

(Continued)

*Primary Examiner* — Natasha E Young
(74) *Attorney, Agent, or Firm* — Osha Bergman Watanabe & Burton LLP

(57) ABSTRACT

An olefin and methanol co-production plant for co-production of an olefin and methanol from a source gas containing methane includes: an olefin production unit for producing the olefin; and a methanol production unit for producing methanol from a carbon oxide gas in the olefin production unit. The olefin production unit includes a partial oxidative coupling device for producing the olefin by partial oxidative coupling reaction of methane contained in the source gas. The methanol production unit includes a reforming device for producing hydrogen by reforming reaction of methane, and a methanol production device for producing methanol by reaction with hydrogen produced by the reforming device. At least one of the reforming device or the methanol production device is configured to perform reaction using the carbon oxide gas in the olefin production unit.

8 Claims, 5 Drawing Sheets

(51) Int. Cl.
  *C07C 2/82* (2006.01)
  *C07C 29/151* (2006.01)

(52) U.S. Cl.
  CPC .................. *C01B 3/34* (2013.01); *C07C 2/82* (2013.01); *B01J 8/04* (2013.01); *B01J 8/0496* (2013.01); *B01J 2208/00504* (2013.01); *B01J 2219/00002* (2013.01); *B01J 2219/0004* (2013.01); *B01J 2219/00038* (2013.01); *C01B 2203/0233* (2013.01); *C01B 2203/0238* (2013.01); *C01B 2203/061* (2013.01); *C01B 2203/1241* (2013.01)

(58) Field of Classification Search
  CPC .. B01J 19/2445; B01J 19/245; B01J 2208/00; B01J 2208/00008; B01J 2208/00017; B01J 2208/00504; B01J 2219/00; B01J 2219/00002; B01J 2219/00027; B01J 2219/00038; B01J 2219/0004; C01B 3/00; C01B 3/02; C01B 3/32; C01B 3/34; C01B 2203/00; C01B 2203/02; C01B 2203/0205; C01B 2203/0227; C01B 2203/0233; C01B 2203/0238; C01B 2203/06; C01B 2203/061; C01B 2203/08; C01B 2203/0805; C01B 2203/0811; C01B 2203/12; C01B 2203/1205; C01B 2203/1211; C01B 2203/1235; C01B 2203/1241; C01B 2203/80; C07C 2/00; C07C 2/76; C07C 2/82; C07C 2/84; C07C 29/00; C07C 29/15; C07C 29/151; C07C 29/1516; C07C 29/1518; C07C 29/152
  See application file for complete search history.

(56) References Cited

U.S. PATENT DOCUMENTS 6,518,476 B1    2/2003   Culp et al.
7,151,198 B2 *  12/2006  Van Egmond .......... C10G 3/49
                                              585/327
2007/0083073 A1 * 4/2007  Bagherzadeh .......... B01J 23/14
                                              502/240
2011/0236293 A1   9/2011  Hardman et al.
2015/0246856 A1   9/2015  Schmigalle et al.
2016/0200643 A1   7/2016  Nyce et al.

FOREIGN PATENT DOCUMENTS

JP    2004-509155 A    3/2004
JP    2015-529230 A   10/2015
RU       2524720 C2    8/2014

OTHER PUBLICATIONS

Proceedings of the 11th International Symposium on Process Systems Engineering, 2012, 410-414, Computer Aided Chemical Engineering vol. 31 (5 pages).
Energy, 2008, 33, 817-833 (17 pages).
Journal of the Japan Petroleum Institute, 1994, 37(2), 112-122 (11 pages).
Journal of Japan Oil Chemists' Society, 1990, 39(12), 1014-1021 (8 pages).
International Search Report of PCT/JP2017/044831, dated Jan. 23, 2018 (10 pages).
International Preliminary Report on Patentability dated Jun. 25, 2020 in corresponding International (PCT) Application No. PCT/JP2017/044831 (11 pages).
Techno-Economic Analysis for Ethylene and Methanol Production from the Oxidative Coupling of Methane Process; 21st European Symposium on Computer Aided Process Engineering (2011) pp. 1874-1878 (5 pages).
Effective heat supply from combustion to reforming in methane reforming with CO2 and O2: comparison between Ni and Pt catalysts; Applied Catalysts A: General 233 (2002) pp. 35-44; URL: https://tohoku.pure.elsevier.com/en/publications/effective-heat-supply-from-combustion-to-reforming-in-methane-ref (11 pages).
The Office Action issued in corresponding Russian Application No. 2020118507, dated Aug. 20, 2020 (9 pages).

* cited by examiner

OLEFIN AND METHANOL CO-PRODUCTION PLANT AND OLEFIN AND METHANOL CO-PRODUCTION METHOD

This application is a national stage application claiming priority to PCT/JP2017/044831, now WO/2019/116484, filed on Dec. 14, 2017.

TECHNICAL FIELD

The present invention relates to an olefin and methanol co-production plant and an olefin and methanol co-production method.

BACKGROUND

As a method for producing olefins such as ethylene and propylene, the MTO (Methanol To Olefin) method is known. In the MTO method, methanol is produced from a source gas (e.g., natural gas) containing methane, and further, olefins are produced from methanol. However, in the MTO method, since olefins are produced via methanol, which is an intermediate product, the total energy consumed for producing olefins is large. Therefore, as a new method for producing olefins, partial oxidative coupling reaction of methane (hereinafter simply referred to as OCM reaction) has been attracting attention.

As a technique for producing olefins using the OCM reaction, a technique disclosed in Patent Document 1 is known. Patent Document 1 describes that olefins are produced from methane using the OCM reaction.

CITATION LIST

Patent Literature

Patent Document 1: US Patent Application Publication No. 2016/0200643 (especially see abstract and claim 1)

SUMMARY

Problems to be Solved

In the OCM reaction, besides olefins, carbon dioxide is produced as a by-product. Since carbon dioxide is a stable compound, it is usually difficult to make good use of the by-produced carbon dioxide. Accordingly, in practice, the by-produced carbon dioxide is discharged outside as it is. However, the emission of carbon dioxide causes global warming. Therefore, it is desired to reduce the emission amount of carbon dioxide.

Further, in the OCM reaction, carbon monoxide is also produced as a by-product. Carbon monoxide is not a greenhouse gas, as it does not absorb much infrared radiation from the earth surface, unlike carbon dioxide. However, when carbon monoxide is irradiated with ultraviolet rays, ozone is generated, and the ozone in the troposphere (tropospheric ozone) causes global warming. Therefore, it is also desired to reduce the emission amount of carbon monoxide.

Under such circumstances, the present inventors have conducted studies and found that a carbon oxide gas, such as carbon monoxide and carbon dioxide, can be used as the source of production of methanol. Therefore, it is conceivable to use a carbon oxide gas which is a by-product of the OCM reaction to produce methanol in order to reduce the emission amount of the carbon oxide gas.

In view of the above, an object of at least one embodiment of the present invention is to provide an olefin and methanol co-production plant and an olefin and methanol co-production method whereby it is possible to produce olefins by the OCM reaction, and simultaneously, it is possible to produce methanol using a carbon oxide gas produced as a by-product of the OCM reaction.

Solution to the Problems (1) An olefin and methanol co-production plant according to some embodiments of the present invention for co-production of an olefin and methanol comprises: an olefin production unit for producing the olefin; and a methanol production unit for producing methanol from a carbon oxide gas in the olefin production unit. The olefin production unit includes a partial oxidative coupling device for producing the olefin by partial oxidative coupling reaction of methane contained in the source gas. The methanol production unit includes a reforming device for producing hydrogen by reforming reaction of methane, and a methanol production device for producing methanol by reaction with hydrogen produced by the reforming device. At least one of the reforming device or the methanol production device is configured to perform reaction using the carbon oxide gas in the olefin production unit.

With the above configuration (1), olefins can be produced directly from methane contained in natural gas by the OCM reaction (partial oxidative coupling), not via methanol as an intermediate product. Thus, it is possible to reduce energy consumed for producing olefins. Further, since methanol can be produced from a carbon oxide gas in the olefin production unit, it is possible to reduce the emission amount of the carbon oxide gas such as carbon monoxide and carbon dioxide. Further, since methanol can be produced from carbon derived from the source gas used for producing olefins, it is unnecessary to separately prepare the source for methanol production from outside. Thus, it is possible to reduce the production cost of methanol.

(2) In some embodiments, in the above configuration (1), the reforming device is configured to produce hydrogen by reforming of methane in the olefin production unit.

With the above configuration (2), hydrogen for methanol production can be produced using methane in the olefin production unit, in addition to the carbon oxide gas. Thus, methanol can be produced using compounds present in the olefin and methanol co-production plant. This eliminates the need to separately supply methane for methanol production, and reduces the amount of the source gas to be used. Thus, it is possible to save the production cost.

(3) In some embodiments, in the above configuration (2), the olefin production unit includes a methane separation device for separating at least methane from a gas in the olefin production unit, and the reforming device is configured to produce hydrogen from methane separated by the methane separation device.

With the above configuration (3), since methane purified through separation by the methane separation device is used, the amount of methane supplied to the reforming device is increased. Thus, it is possible to enhance the reforming reaction, and it is possible to increase the production amount of hydrogen.

(4) In some embodiments, in any one of the above configurations (1) to (3), the olefin production unit includes a methanation device for producing methane from the carbon oxide gas in the olefin production unit, and the reforming device is configured to produce hydrogen from methane produced by the methanation device.

With the above configuration (4), the concentration of methane is increased by the methanation device, and the amount of methane supplied to the reforming device is increased. Thus, it is possible to enhance the reforming reaction, and it is possible to increase the production amount of hydrogen. Further, since the production amount of hydrogen is increased, it is possible to increase the production amount of methanol.

(5) In some embodiments, in any one of the above configurations (1) to (4), the olefin production unit includes a methanation device for producing methane from the carbon oxide gas in the olefin production unit, and the partial oxidative coupling device is configured to produce the olefin from methane produced by the methanation device.

With the above configuration (5), the concentration of methane is increased by the methanation device, and the amount of methane supplied to the partial oxidative coupling device is increased. Thus, it is possible to enhance the OCM reaction using methane, and it is possible to increase the production amount of olefins.

(6) In some embodiments, in any one of the above configurations (1) to (5), the reforming device is configured to produce hydrogen by reforming the source gas.

With the above configuration (6), since hydrogen can be obtained directly from the source gas by the reforming device, it is possible to easily obtain hydrogen.

(7) In some embodiments, in any one of the above configurations (1) to (6), the methanol production unit includes a combustion device for combusting a fuel to generate heat used for the reforming in the reforming device, and at least one of the reforming device or the methanol production device is configured to perform reaction using a carbon oxide gas produced by the combusting device.

With the above configuration (7), at least one of the methane reforming or the methanol production can be performed using the carbon oxide gas produced by the combustion device while using heat generated by the combustion device in the reforming device. Further, the amount of the carbon oxide gas supplied from the olefin production unit to the methanol production unit can be reduced. As a result, even if the production amount of the carbon oxide gas is reduced to increase the yield of olefins in the olefin production unit, it is possible to cover the amount of the carbon oxide gas required by the methanol production unit.

(8) An olefin and methanol co-production method according to some embodiments of the present invention for co-production of an olefin and methanol comprises: a partial oxidative coupling step of producing the olefin by partial oxidative coupling reaction of methane contained in the source gas; a reforming step of producing hydrogen by reforming reaction of methane; and a methanol production step of producing methanol by reaction with hydrogen produced in the reforming step. At least one of the reforming step or the methanol production step includes reaction using a carbon oxide gas produced in the partial oxidative coupling step.

With the above configuration (8), olefins can be produced directly from methane contained in natural gas by the OCM reaction (partial oxidative coupling), not via methanol as an intermediate product. Thus, it is possible to reduce energy consumed for producing olefins. Further, since methanol can be produced from a carbon oxide gas obtained in the partial oxidative coupling step, it is possible to reduce the emission amount of the carbon oxide gas such as carbon monoxide and carbon dioxide. Further, since methanol can be produced from carbon derived from natural gas used for producing olefins, it is unnecessary to separately prepare the source for methanol production from outside. Thus, it is possible to reduce the production cost of methanol.

Advantageous Effects

According to at least one embodiment of the present invention, there is provided an olefin and methanol co-production plant and an olefin and methanol co-production method whereby it is possible to produce olefins by the OCM reaction, and simultaneously, it is possible to produce methanol using a carbon oxide gas produced as a by-product of the OCM reaction.

DETAILED DESCRIPTION

Embodiments of the present invention will now be described in detail with reference to the accompanying drawings. However, the following embodiments and the drawings are illustrative only, and various modifications may be applied as long as they do not depart from the object of the present invention. Further, two or more embodiments may be optionally combined in any manner.

It is intended, however, that unless particularly specified, dimensions, materials, shapes, relative positions and the like of components described in the embodiments shall be interpreted as illustrative only and not intended to limit the scope of the present invention.

For instance, an expression of relative or absolute arrangement such as "in a direction", "along a direction", "parallel", "orthogonal", "centered", "concentric" and "coaxial" shall not be construed as indicating only the arrangement in a strict literal sense, but also includes a state where the arrangement is relatively displaced by a tolerance, or by an angle or a distance whereby it is possible to achieve the same function.

For instance, an expression of an equal state such as "same" "equal" and "uniform" shall not be construed as indicating only the state in which the feature is strictly equal, but also includes a state in which there is a tolerance or a difference that can still achieve the same function.

Further, for instance, an expression of a shape such as a rectangular shape or a cylindrical shape shall not be construed as only the geometrically strict shape, but also includes a shape with unevenness or chamfered corners within the range in which the same effect can be achieved.

On the other hand, an expression such as "comprise", "include", "have", "contain" and "constitute" are not intended to be exclusive of other components.

Figure 1:
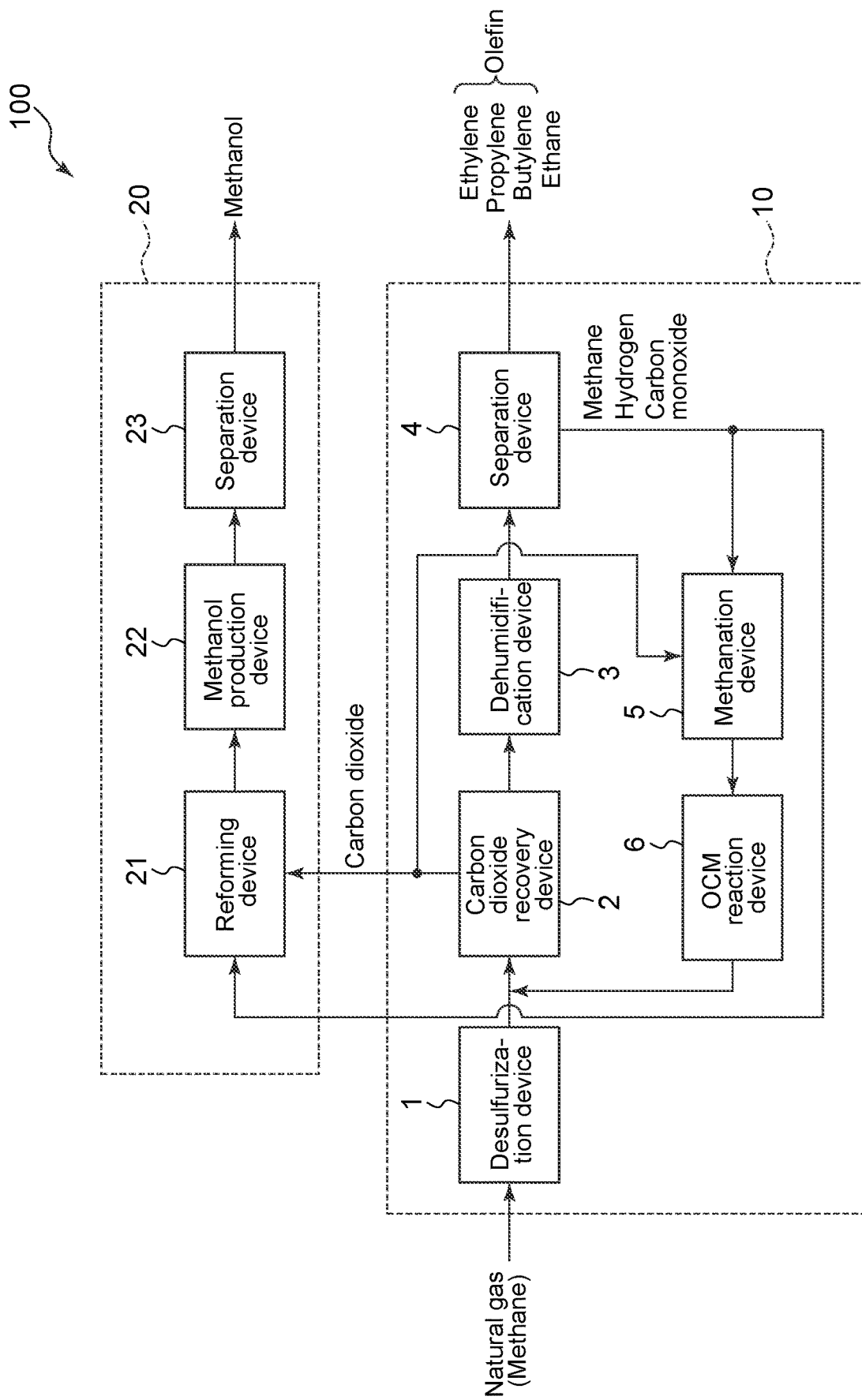
FIG. 1 is a system diagram of an olefin and methanol co-production plant according to a first embodiment of the present invention.

FIG. 1 is a system diagram of an olefin and methanol co-production plant 100 according to a first embodiment of the present invention. The co-production plant 100 is configured to simultaneously produce an olefin and methanol from natural gas (source gas containing methane). The co-production plant 100 includes an olefin production unit 10 for producing an olefin (ethylene, propylene, butylene, etc.) and a methanol production unit 20 for producing methanol from a carbon oxide gas (at least one of carbon monoxide or carbon dioxide, the same shall apply hereinafter) in the olefin production unit 10.

The olefin production unit 10 includes a desulfurization device 1, a carbon dioxide recovery device 2, a dehumidification device 3, a separation device 4, a methanation device 5, and an OCM reaction device 6.

The desulfurization device 1 is configured to remove sulfur components contained in natural gas. Illustrative examples of the sulfur components include hydrogen sulfide. As a specific configuration of the desulfurization device 1, there may be mentioned an adsorbent for adsorbing sulfur components in natural gas.

The carbon dioxide recovery device 2 is configured to separate and recover carbon dioxide in the olefin production unit 10 (specifically, carbon dioxide contained in natural gas and carbon dioxide (carbon oxide gas) produced by the OCM reaction device 6 described later) from a circulating gas. The circulating gas in this context means a gas that flows through a passage running from the carbon dioxide recovery device 2, passing through the dehumidification device 3, the separation device 4, the methanation device 5, and the OCM reaction device 6, and returned to the carbon dioxide recovery device 2. By recovering carbon dioxide with the carbon dioxide recovery device 2, it is possible to prevent solidification of carbon dioxide (i.e., production of dry ice) in freezing in the separation device 4 described later.

The recovery of carbon dioxide with the carbon dioxide recovery device 2 can be performed by, for instance, bringing an alkaline aqueous solution into contact with the gas. The recovered carbon dioxide is separated from the alkaline aqueous solution by, for instance, heating of the alkaline aqueous solution, and is then supplied to a reforming device 21, which will be described later, and the methanation device 5.

The dehumidification device 3 is configured to remove water in the olefin production unit 10 (specifically, steam contained in natural gas and water produced by the OCM reaction device 6 described later, etc.) from the circulating gas. By dehumidification with the dehumidification device 3, it is possible to prevent solidification of water (i.e., production of ice) in freezing in the separation device 4 described later. The recovery of water in the dehumidification device 3 can be performed by, for instance, bringing the gas into contact with a desiccant.

The separation device 4 may be, for example, a distillation tower, which is configured to separate and recover methane, hydrogen, and carbon monoxide from the gas using a difference in boiling point, by cooling and then supplying the gas to the distillation tower. The hydrogen and carbon monoxide separated and recovered here include hydrogen and carbon monoxide produced by the OCM reaction device 6 described later.

In the separation device 4, the gas is cooled to about $-90°$ C. to $-120°$ C. When the gas is cooled to this temperature range, methane, hydrogen, and carbon monoxide in the gas are separated and recovered in the form of gas. The recovered mixed gas of methane, hydrogen, and carbon monoxide is supplied to the later-described methanation device 5 and to the reforming device 21.

On the other hand, the separation device 4 is supplied with natural gas, which is fed from outside, and with reaction gas produced in the OCM reaction device 6 via the carbon dioxide recovery device 2 and the dehumidification device 3. Accordingly, the separation device 4 is supplied with ethane and olefins such as ethylene, propylene, and butylene manufactured (produced) by the OCM reaction device 6. Therefore, when the gas is cooled to the above temperature range in the separation device 4, the other components (e.g., olefins, ethane) in the gas are also liquefied. This allows separation and recovery of the other components. The recovered other components are further separated by a separation tower (not shown) individually. As a result, substances such as olefins are obtained as final products.

As the separation device 4, for example, a freezer using both ethylene refrigerant and propylene refrigerant can be used.

The methanation device 5 is configured to produce methane from a carbon oxide gas (at least one of carbon monoxide or carbon dioxide) in the olefin production unit 10. More specifically, the methanation device 5 converts a part of carbon dioxide recovered by the carbon dioxide recovery device 2 and carbon monoxide produced by the OCM reaction device 6 (described later) and separated and recovered by the separation device 4 into methane.

A catalyst (methanation catalyst) for the methanation reaction may be any methanation catalyst. Examples of the methanation catalyst include nickel catalysts. Reaction conditions may be, for example, $220°$ C. to $510°$ C. and 0 MPa to 3.0 Mpa approximately at the outlet of a catalytic layer placed in the methanation device 5.

In this reaction, as described above, the methanation device 5 is supplied with a part of carbon dioxide recovered by the carbon dioxide recovery device 2. The amount of carbon dioxide supplied to the methanation device 5 may be constant at all times or may vary as appropriate. For instance, when the amount of carbon dioxide supplied to the methanation device 5 is constant, the amount of carbon dioxide supplied to the methanol production unit 20 is, for example, 0.1 or more and 2.0 or less, preferably 0.5 or more and 1.5 or less, more preferably 0.8 or more and 1.2 or less, particularly preferably about 1, in terms of a value obtained by dividing the amount of substance of carbon dioxide by the amount of substance of methane.

When the amount of carbon dioxide supplied to the methanation device 5 varies as appropriate, the following may be applied: In the co-production plant 100, as described later in detail, the reforming device 21 is supplied with carbon dioxide, and the reforming device 21 produces carbon monoxide and hydrogen from methane and carbon dioxide. Further, the methanol production device 22 disposed downstream of the reforming device 21 produces methanol from carbon monoxide and carbon dioxide. Therefore, by measuring the amount of methane supplied to the reforming device 21 and calculating the amount of carbon dioxide used in the reforming device 21, the excess of carbon dioxide can be supplied to the methanation device 5. Thus, it is possible to produce olefins using excess carbon dioxide while increasing the production amount of methanol.

On the other hand, thorough investigation by the inventors has shown that as the mole ratio of oxygen to methane increases in the OCM reaction device 6 downstream of the methanation device 5, more carbon dioxide is produced as a by-product in the OCM reaction device 6. Therefore, it is preferable to increase methane in order to reduce the mole ratio of oxygen to methane (specifically, for example, 0.5 or less in terms of mole ratio obtained by dividing the amount of substance of oxygen by the amount of substance of methane). In view of this, the methanation device 5 may be supplied with carbon dioxide so as to increase the amount of methane supplied to the OCM reaction device 6 (such that the mole ratio is 0.5 or less in the OCM reaction device 6, for example). More specifically, for example, the concentration of oxygen may be measured, and the methanation device 5 may be supplied with carbon dioxide in an amount such that the above mole ratio is about 0.2 to 0.4, and the remainder may be supplied to the reforming device 21. Thus, it is possible to suppress by-production of carbon dioxide and increase the production amount of olefins.

The OCM reaction device 6 (partial oxidative coupling device) is configured to produce olefins by OCM reaction of methane contained in natural gas. More specifically, the OCM reaction device 6 produces olefins from methane (including methane in natural gas) separated and recovered by the separation device 4 and methane produced by the methanation device 5. In the OCM reaction device 6, in addition to olefins such as ethylene, propylene, and butylene, a carbon oxide gas such as carbon monoxide and carbon dioxide and ethane are also produced. The produced olefins, carbon oxide gas, ethane, etc. are supplied to the carbon dioxide recovery device 2.

In the OCM reaction device 6, first, methyl radicals are produced from methane and oxygen. The produced methyl radicals react with each other and produce ethane. Then, two hydrogen atoms are removed from ethane, so that ethylene and hydrogen (molecules) are produced. In addition, methyl radicals produced in the middle of reaction react with ethylene to produce propylene. Furthermore, methyl radicals produced in the middle of reaction react with propylene to produce butylene. In addition to these, as the oxidation further proceeds, a carbon oxide gas such as carbon monoxide and carbon dioxide is produced.

By using methane produced by the methanation device 5 for the OCM reaction in the OCM reaction device 6, since the concentration of methane is increased by the methanation device 5, the amount of methane supplied to the OCM reaction device 6 is increased. Thus, it is possible to enhance the OCM reaction using methane, and it is possible to increase the production amount of olefins.

A catalyst (OCM reaction catalyst) for the OCM reaction may be any OCM reaction catalyst. As the OCM reaction catalyst, a catalyst disclosed in the U.S. Pat. No. 8,962,517 may be used. Reaction conditions may be, for example, 450° C. to 600° C. approximately at the inlet of a catalytic layer placed in the OCM reaction device 6.

The methanol production unit 20 includes a reforming device 21, a methanol production device 22, and a separation device 23.

The reforming device 21 is configured to produce hydrogen by reforming reaction of methane. More specifically, the reforming device 21 produces hydrogen by reforming methane separated and recovered by the separation device 4. By reforming methane in the olefin production unit 10 to produce hydrogen, hydrogen for methanol production can be produced using methane in the olefin production unit 10, in addition to carbon dioxide. Thus, methanol can be produced using compounds present in the co-production plant 100. This eliminates the need to separately supply methane for methanol production and reduces the amount of natural gas to be used. Thus, it is possible to save the production cost.

In particular, in the co-production plant 100, a part of the gas circulating in the olefin production unit 10 is extracted and used in the reforming device 21. Accordingly, the amount of the gas circulating in the olefin production unit 10 is reduced. Thus, it is possible to reduce drive energy of a compressor (not shown) for circulating the olefin production unit 10.

The olefin production unit 10 includes the separation device 4 (methane separation device) for separating methane from the gas in the olefin production unit 10. The reforming device 21 produces hydrogen from methane separated by the separation device 4. In this way, since methane purified through separation by the separation device 4 is used, the amount of methane supplied to the reforming device 21 is increased. Thus, it is possible to enhance the reforming reaction, and it is possible to increase the production amount of hydrogen.

The reforming device 21 is supplied with carbon dioxide recovered by the carbon dioxide recovery device 2 (i.e., carbon dioxide in the olefin production unit 10). Since the reforming is performed in the presence of carbon dioxide, carbon potential is increased, and the following reaction equation (1) proceeds.

$$3CH_4 + CO_2 + 2H_2O \rightarrow 4CO + 8H_2 \qquad \text{reaction equation (1)}$$

As shown by the reaction equation (1), 3 mol of methane produces 4 mol of carbon monoxide. Accordingly, in the subsequent methanol production device 22, 4 mol of carbon monoxide produces 4 mol of methanol.

Although described in detail later, in the methanol production device 22 downstream of the reforming device 21, 2 mol of hydrogen is used per 1 mol of carbon monoxide to produce methanol. Therefore, in the reforming device 21, when the mole ratio of the produced carbon monoxide to hydrogen is 1:2 as shown in the reaction equation (1), the composition of the source gas for methanol production approximates the theoretical ratio.

The reforming in the reforming device 21 is steam reforming. Accordingly, in the reforming device 21, hydrogen is produced by reaction of steam and methane at high temperature and high pressure. Reforming conditions may be, for example, 900° C. to 1000° C. and 0 MPa to 3.5 Mpa approximately at the outlet of a catalytic layer placed in the reforming device 21. The reforming can be performed with any reforming catalyst. As the reforming catalyst, an oxide of transition metal such as nickel and platinum can be used.

The methanol production device 22 is configured to produce methanol by reaction with hydrogen produced by the reforming device 21. In the methanol production device 22, methanol is produced from hydrogen produced by the reforming device 21 and carbon monoxide and carbon dioxide discharged from the reforming device 21. More specifically, 2 mol of hydrogen and 1 mol of carbon monoxide produce 1 mol of methanol. Further, 3 mol of hydrogen and 1 mol of carbon dioxide produce 1 mol of methanol.

Here, carbon monoxide and carbon dioxide discharged from the reforming device 21 and supplied to the methanol production device 22 include unreacted carbon monoxide and carbon dioxide. The unreacted carbon monoxide discharged from the reforming device 21 includes carbon monoxide separated and recovered together with methane by the separation device 4. Further, the unreacted carbon dioxide discharged from the reforming device 21 includes carbon dioxide separated and recovered by the carbon dioxide recovery device 2.

Accordingly, in the methanol production device 22, methanol is produced from carbon monoxide separated and recovered by the separation device 4 and carbon monoxide produced by the reforming device 21 (see the reaction equation (1)). Further, in the methanol production device 22, methanol is directly produced from unreacted carbon dioxide in the reforming device 21. Thus, by using both carbon monoxide and carbon dioxide, it is possible to increase the production amount of methanol.

In the reforming device 21 upstream of the methanol production device 22, as shown by the reaction equation (1), carbon dioxide is consumed to produce carbon monoxide. As a result, the gas supplied to the methanol production device 22 contains a relatively high amount of carbon monoxide and a relatively low amount of carbon dioxide. Accordingly, in the methanol production device 22, mainly, methanol is produced from carbon monoxide.

Regarding methanol production conditions, for example, a mixed gas of hydrogen, carbon monoxide, and carbon dioxide may be caused to react at 200° C. to 350° C. at 5 MPa to 25 MPa approximately, using any catalyst. Examples of the catalyst include a composite catalyst of copper, zinc oxide, and aluminum oxide.

The separation device 23 is configured to separate and recover methanol from the reaction liquid (containing methanol) discharged from the methanol production device 22. As the separation device 23, for example, a distillation tower using difference in boiling point can be used. Thereby, methanol is obtained as final products.

Operation control of the co-production plant 100 is performed by a control device not depicted. The control device includes a central processing unit (CPU), a random access memory (RAM), a read only memory (ROM), a hard disk drive (HDD), and a control circuit, not depicted, and is realized by executing a predetermined control program stored in the ROM by the CPU.

With the co-production plant 100 having the above configuration, olefins can be produced directly from methane contained in natural gas by the OCM reaction, not via methanol as an intermediate product. Thus, it is possible to reduce energy consumed for producing olefins. Further, since methanol can be produced from a carbon oxide gas in the olefin production unit 10, it is possible to reduce the emission amount of the carbon oxide gas such as carbon monoxide and carbon dioxide. Further, since methanol can be produced from carbon derived from natural gas used for producing olefins, it is unnecessary to separately prepare the source for methanol production from outside. Thus, it is possible to reduce the production cost of methanol.

Although in the above example, the reforming device 21 is configured to perform the reforming using hydrogen in the olefin production unit 10, the reforming device 21 may be configured to produce hydrogen by reforming natural gas (source gas). In other words, although not depicted, a pipe connecting a supply system of natural gas and the reforming device 21 may be provided, and the reforming may be performed using natural gas supplied through the pipe. Thus, since hydrogen can be obtained directly from the source gas by the reforming device 21, it is possible to easily obtain hydrogen.

Further, although in the above example, the reforming device 21 is supplied with carbon dioxide in the olefin production unit 10, in addition to or instead of the reforming device 21, the methanol production device 22 may be directly supplied with carbon dioxide in the olefin production unit 10. In this case, the methanol production device 22 produces methanol from hydrogen produced by the reforming device 21 and carbon dioxide recovered by the carbon dioxide recovery device 2. Further, in the reforming device 21, 1 mol of carbon monoxide and 3 mol of hydrogen are produced from 1 mol of methane and 1 mol of water.

Further, although in the above example, the reforming device 21 is supplied with carbon monoxide in the olefin production unit 10, if the reforming device 21 is separately supplied with methane, in addition to or instead of the reforming device 21, the methanol production device 22 may be directly supplied with carbon monoxide in the olefin production unit 10.

Figure 2:
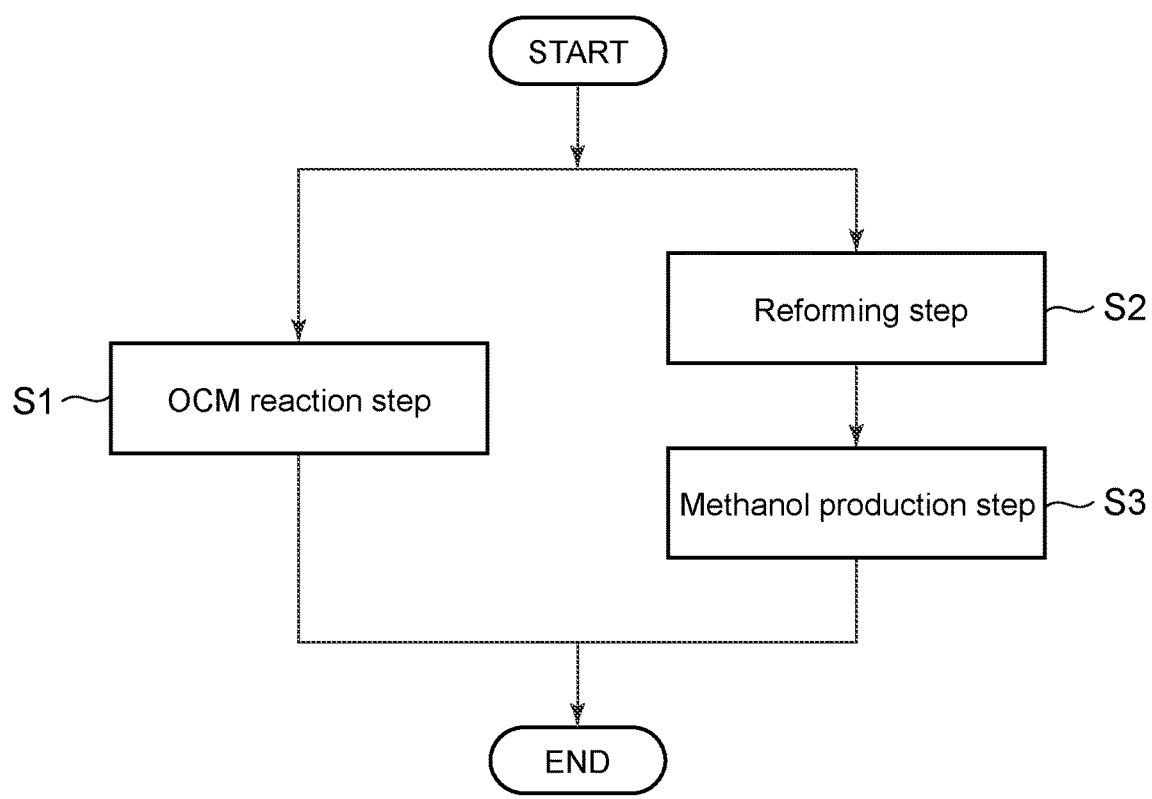
FIG. 2 is a flowchart of an olefin and methanol co-production method according to an embodiment of the present invention.

FIG. 2 is a flowchart of an olefin and methanol co-production method according to an embodiment of the present invention (hereinafter, also simply referred to as "co-production method according to an embodiment"). Since this flowchart is performed in the co-production plant 100, FIG. 2 will be described with reference to FIG. 1 as appropriate. Also, this flowchart is performed with the above control device.

The co-production method according to this embodiment includes an OCM reaction step S1 (partial oxidative coupling step), a reforming step S2, and a methanol production step S3. However, other steps such as a methanation step and a separation step may also be included, if necessary.

In the OCM reaction step S1, an olefin is produced by OCM reaction (partial oxidative coupling reaction) of methane contained in natural gas (source gas). The OCM reaction step S1 is performed in the OCM reaction device 6. The olefin produced in the OCM reaction step S1 is taken out of the co-production plant 100.

Methane used in the OCM reaction step S1 includes methane contained in natural gas and methane produced by the methanation device 5. Further, methane used in the OCM reaction device 6 includes methane that is first supplied to the OCM reaction device 6, but does not react and is discharged from the OCM reaction device 6 and returned through the carbon dioxide recovery device 2, the dehumidification device 3, the separation device 4, and the methanation device 5. Thus, in the OCM reaction step S1, the OCM reaction is performed using methane in the olefin production unit 10.

OCM reaction conditions may be the reaction conditions described above regarding the OCM reaction device 6.

In the reforming step S2, hydrogen is produced by reforming reaction of methane. The reforming step S2 is performed in the reforming device 21. In the reforming step S2, steam reforming of methane is performed using a gas (containing methane, hydrogen, carbon monoxide, etc.) discharged from the separation device 4 and carbon dioxide recovered by the carbon dioxide recovery device 2. The reforming produces a gas containing hydrogen, carbon monoxide, and carbon dioxide. Specific reaction mechanism and reaction conditions are the same as those described above regarding the reforming device 21.

In the methanol production step S3, methanol is produced from hydrogen produced in the reforming step S2 and carbon monoxide and carbon dioxide (including unreacted carbon monoxide and carbon dioxide) produced in the reforming step S2. Specific reaction conditions are the same as those described above regarding the reforming device 21. The methanol produced in the methanol production step S3 is taken out of the co-production plant 100.

According to the co-production method described above, olefins can be produced directly from methane contained in natural gas by the OCM reaction (partial oxidative coupling), not via methanol as an intermediate product. Thus, it is possible to reduce energy consumed for producing olefins.

Further, since methanol can be produced from a carbon oxide gas in the OCM reaction step S1, it is possible to reduce the emission amount of the carbon oxide gas such as carbon monoxide and carbon dioxide. Further, since methanol can be produced from carbon derived from the source gas used for producing olefins, it is unnecessary to separately prepare the source for methanol production from outside. Thus, it is possible to reduce the production cost of methanol.

Although in the above example, the carbon oxide gas in the OCM reaction step S1 is used for reaction in the reforming step S2, the carbon oxide gas in the OCM reaction step S1 may be used for the reaction in the methanol production step S3. Thus, in the methanol production step S3, methanol can be produced from hydrogen obtained in the reforming step S2 and the carbon oxide gas in the OCM reaction step S1. In addition, the carbon oxide gas in the OCM reaction process S1 can be used for both reactions in the reforming step S2 and the methanol production step S3.

Figure 3:
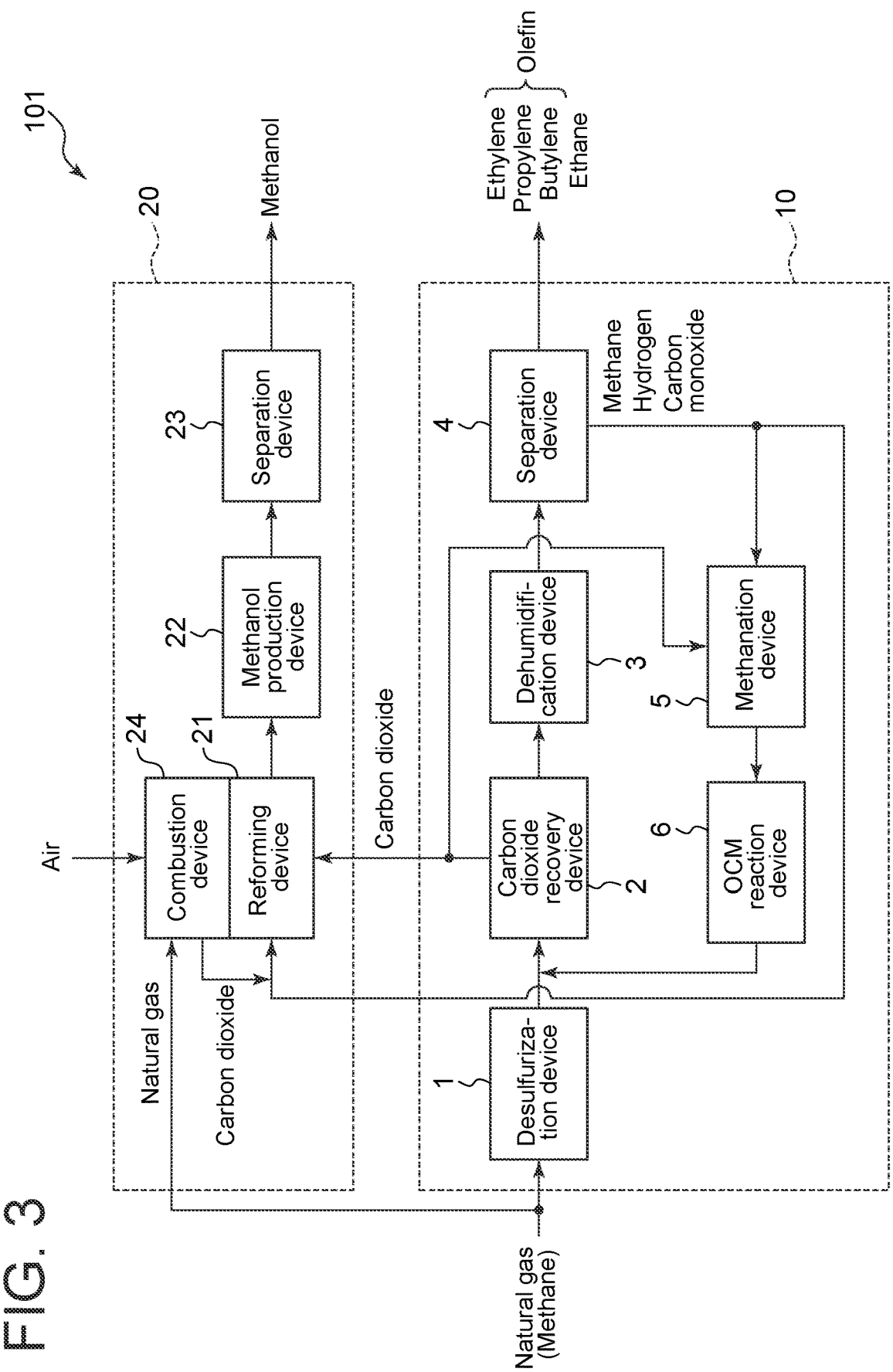
FIG. 3 is a system diagram of an olefin and methanol co-production plant according to a second embodiment of the present invention.

FIG. 3 is a system diagram of an olefin and methanol co-production plant 101 according to a second embodiment of the present invention. In the following description, points different from the co-production plant 100 shown in FIG. 1 will be mainly described, and points common to the co-production plant 100 will not be described for simplification of description.

In the co-production plant 101, the methanol production unit 20 includes a combustion device 24 for combusting natural gas (fuel) to generate heat used for reforming in the reforming device 21. The methanol production device 22 is configured to produce methanol from a carbon oxide gas produced by the combustion device 24. The carbon oxide gas in this context includes carbon dioxide produced by full combustion, and carbon monoxide produced by incomplete combustion.

With the combustion device 24, at least one of the methane reforming or the methanol production can be performed using the carbon oxide gas produced by the combustion device 24 while using heat generated by the combustion device 24 in the reforming device 21. Further, the amount of the carbon oxide gas supplied from the olefin production unit 10 to the methanol production unit 20 can be reduced. As a result, even if the production amount of the carbon oxide gas is reduced to increase the yield of olefins in the olefin production unit 10, it is possible to cover the amount of the carbon oxide gas including carbon dioxide required by the methanol production unit 20.

In the example shown in FIG. 3, as with the co-production plant 100, the methanol production device 22 can produce methanol by reaction with carbon dioxide in the olefin production unit 10. In addition, both the reforming device 21 and the methanol production device 22 can perform reaction with carbon dioxide in the olefin production unit 10.

Figure 4:
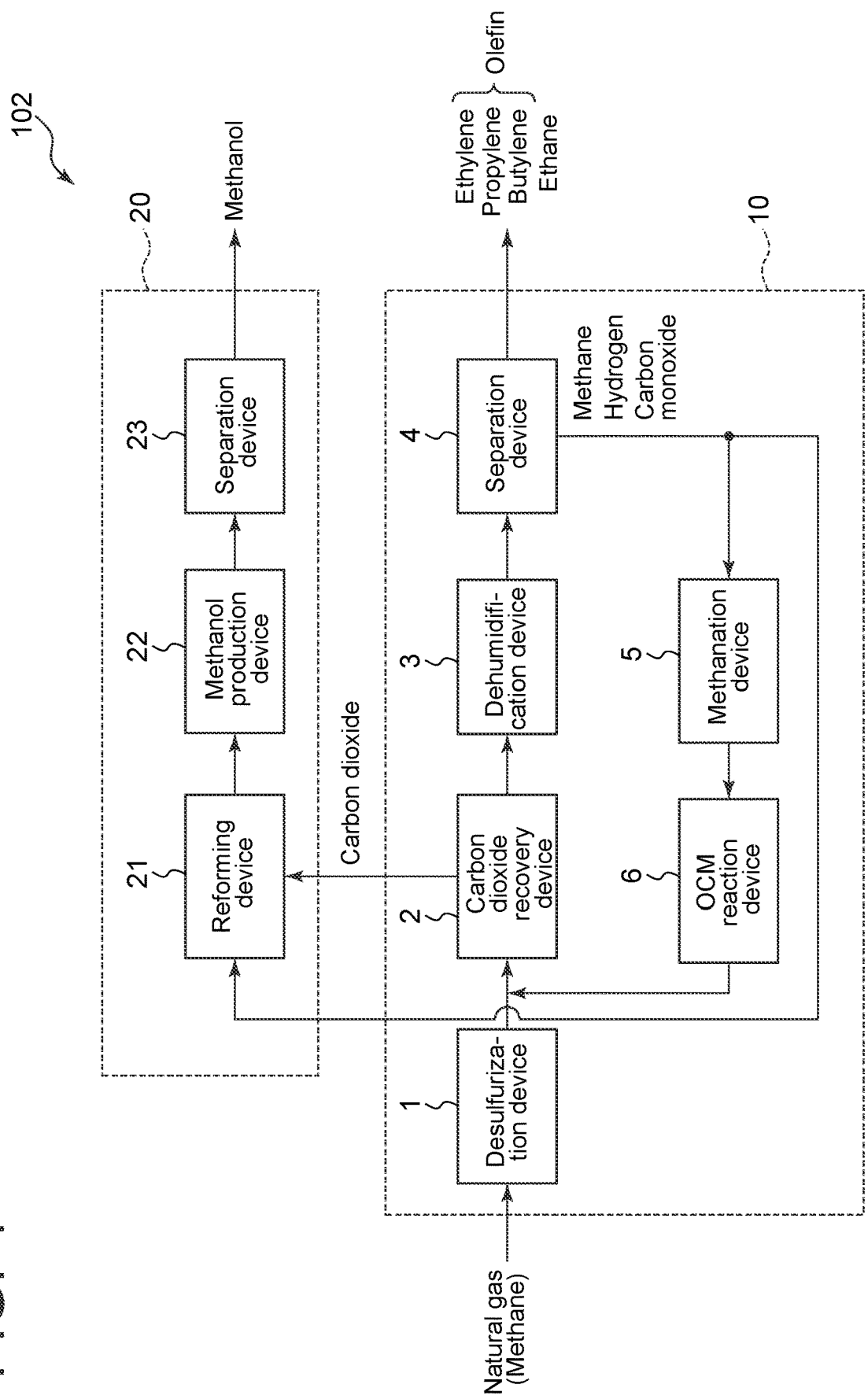
FIG. 4 is a system diagram of an olefin and methanol co-production plant according to a third embodiment of the present invention.

FIG. 4 is a system diagram of an olefin and methanol co-production plant 102 according to a third embodiment of the present invention. In the following description, points different from the co-production plant 100 shown in FIG. 1 will be mainly described, and points common to the co-production plant 100 will not be described for simplification of description.

In the co-production plant 102, the entire amount of carbon dioxide recovered by the carbon dioxide recovery device 2 is supplied to the reforming device 21. In other words, in the co-production plant 102, unlike the co-production plant 100, carbon dioxide recovered by the carbon dioxide recovery device 2 is not supplied to the methanation device 5.

Thus, the entire amount of carbon dioxide in the olefin production unit 10 is supplied to the reforming device 21, so that the production amount of carbon monoxide and hydrogen according to the above equation (1) can be increased. Consequently, it is possible to increase the production amount of methanol in the methanol production device 22, and it is possible to increase the production amount of methanol in the co-production plant 102.

In the example shown in FIG. 4, as with the co-production plant 100, the methanol production device 22 can produce methanol by reaction with carbon dioxide in the olefin production unit 10. In addition, both the reforming device 21 and the methanol production device 22 can perform reaction with carbon dioxide in the olefin production unit 10.

Figure 5:
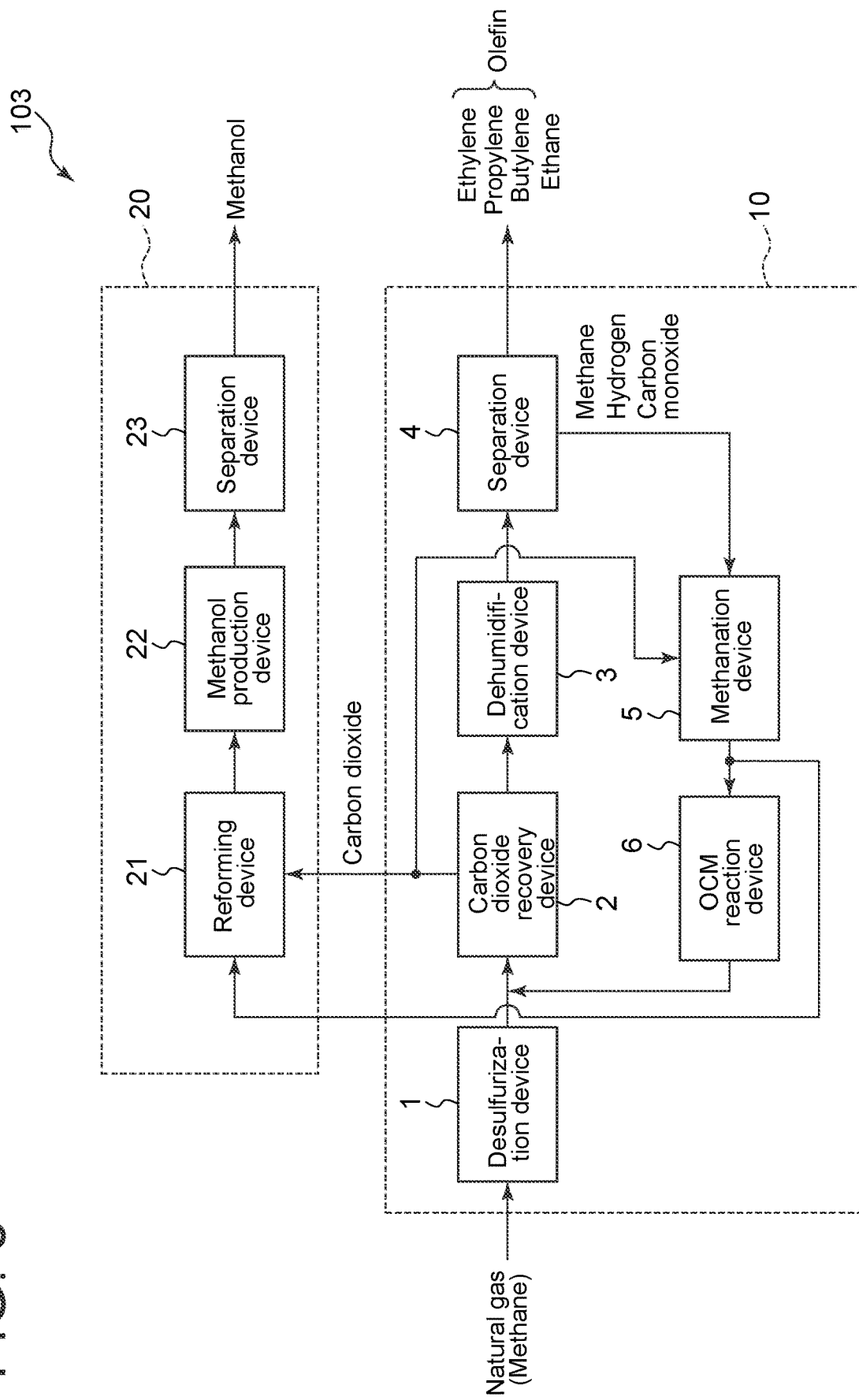
FIG. 5 is a system diagram of an olefin and methanol co-production plant according to a fourth embodiment of the present invention.

FIG. 5 is a system diagram of an olefin and methanol co-production plant 103 according to a fourth embodiment of the present invention. In the following description, points different from the co-production plant 100 shown in FIG. 1 will be mainly described, and points common to the co-production plant 100 will not be described for simplification of description.

In the co-production plant 103, a gas between the methanation device 5 and the OCM reaction device 6 is supplied to the reforming device 21. In other words, although in the co-production plant 100, the gas before methanation by the methanation device 5 is supplied to the reforming device 21, in the co-production plant 103 shown in FIG. 5, the gas after methanation is supplied to the reforming device 21. Thus, the reforming device 21 is configured to produce hydrogen from methane produced by the methanation device 5.

Accordingly, the concentration of methane is increased by the methanation device 5, and the amount of methane supplied to the reforming device 21 is increased. Thus, it is possible to enhance the reforming reaction, and it is possible to increase the production amount of hydrogen. Further, since the production amount of hydrogen is increased, it is possible to increase the production amount of methanol. Moreover, by methanizing carbon monoxide, which is a carbon oxide gas that does not contribute to production of olefin, it is possible to reduce the emission of carbon monoxide, and to make effective use of carbon monoxide. Furthermore, by methanizing carbon dioxide of the carbon oxide gas, even if there is carbon dioxide in an amount that cannot be used in the methanol production unit 20, carbon dioxide can be converted to methane and used for reforming.

In the example shown in FIG. 5, as with the co-production plant 100, the methanol production device 22 can produce methanol by reaction with carbon dioxide in the olefin production unit 10. In addition, both the reforming device 21 and the methanol production device 22 can perform reaction with carbon dioxide in the olefin production unit 10.

REFERENCE SIGNS LIST

1 Desulfurization device
2 Carbon dioxide recovery device
3 Device
4 Separation device (Methane separation device)
5 Methanation device
6 OCM reaction device
10 Olefin production unit
20 Methanol production unit
21 Reforming device
22 Methanol production device
23 Separation device
24 Combustion device
100, 101, 102, 103 Co-production plant

The invention claimed is:

1. An olefin and methanol co-production plant for co-production of an olefin and methanol from a source gas containing methane, comprising:
   an olefin production unit for producing the olefin; and
   a methanol production unit for producing methanol from a carbon oxide gas in the olefin production unit,
   wherein the olefin production unit includes a partial oxidative coupling device for producing the olefin by partial oxidative coupling reaction of methane contained in the source gas,
   wherein the methanol production unit includes
      a reforming device for producing hydrogen by reforming reaction of methane, and
      a methanol production device for producing methanol by reaction with hydrogen produced by the reforming device, and
   wherein at least one of the reforming device or the methanol production device is configured to perform reaction using the carbon oxide gas in the olefin production unit.

2. The olefin and methanol co-production plant according to claim 1,
   wherein the reforming device is configured to produce hydrogen by reforming of methane in the olefin production unit.

3. The olefin and methanol co-production plant according to claim 1,
   wherein the olefin production unit includes a methane separation device for separating at least methane from a gas in the olefin production unit, and
   wherein the reforming device is configured to produce hydrogen from methane separated by the methane separation device.

4. The olefin and methanol co-production plant according to claim 1,
   wherein the olefin production unit includes a methanation device for producing methane from the carbon oxide gas in the olefin production unit, and
   wherein the reforming device is configured to produce hydrogen from methane produced by the methanation device.

5. The olefin and methanol co-production plant according to claim 1,
   wherein the olefin production unit includes a methanation device for producing methane from the carbon oxide gas in the olefin production unit, and
   wherein the partial oxidative coupling device is configured to produce the olefin from methane produced by the methanation device.

6. The olefin and methanol co-production plant according to claim 1,
   wherein the reforming device is configured to produce hydrogen by reforming the source gas.

7. The olefin and methanol co-production plant according to claim 1,
   wherein the methanol production unit includes a combustion device for combusting a fuel to generate heat used for the reforming in the reforming device, and
   wherein at least one of the reforming device or the methanol production device is configured to perform reaction using a carbon oxide gas produced by the combusting device.

8. An olefin and methanol co-production method for co-production of an olefin and methanol from a source gas containing methane, comprising:
   a partial oxidative coupling step of producing the olefin by partial oxidative coupling reaction of methane contained in the source gas;
   a reforming step of producing hydrogen by reforming reaction of methane; and
   a methanol production step of producing methanol by reaction with hydrogen produced in the reforming step,
   wherein at least one of the reforming step or the methanol production step includes reaction using a carbon oxide gas produced in the partial oxidative coupling step.

* * * * *